United States Patent
Littlewood et al.

(12)

(10) Patent No.: US 6,506,939 B1
(45) Date of Patent: Jan. 14, 2003

(54) PRODUCTION OF ACRYLIC MONOMERS

(75) Inventors: Peter Stuart Littlewood, Ilkley (GB); Michael Singh, Pudsey (GB)

(73) Assignee: Ciba Specialty Chemicals Water Treatments Ltd., Bradford (GB)

( * ) Notice: Subject to any disclaimer, the term of this patent is extended or adjusted under 35 U.S.C. 154(b) by 0 days.

(21) Appl. No.: 09/889,281

(22) PCT Filed: Jan. 12, 2000

(86) PCT No.: PCT/EP00/00162

§ 371 (c)(1),
(2), (4) Date: Jul. 13, 2001

(87) PCT Pub. No.: WO00/41996

PCT Pub. Date: Jul. 20, 2000

(30) Foreign Application Priority Data

Jan. 16, 1999  (GB) ............................................. 9900875

(51) Int. Cl.$^7$ ........................................... C07C 233/09
(52) U.S. Cl. ..................... 564/205; 564/205; 544/114; 544/176
(58) Field of Search ................................ 564/204, 205; 544/114, 176

(56) References Cited

U.S. PATENT DOCUMENTS 5,639,840 A * 6/1997 Fife et al. .................... 564/204

FOREIGN PATENT DOCUMENTS

EP           0619295       10/1994

OTHER PUBLICATIONS

Patent Abstracts of Japan vol. 1996, No. 04 for JP 07316111 (1996).
T. Mitsudo et al., Tetrahendron Lett. (1992), 33(38), pp. 5533–5536.
Patent Abstracts of Japan vol. 016, No. 443 for JP 04154749 (1992).
Chem. Abstr. 123: 316553 for J. Elastomers Plast., (1995), 27(3), pp. 223–238.
Patent Abstracts of Japan vol. 1999, No. 01, for JP 10279545 (1999).
Patent Abstracts of Japan vol. 015, No. 080, for JP 02304071 (1991).
Journal of the American Chemical Society, vol. 101, No. 12, (1979), pp. 3283–3288.
Patent Abstracts of Japan vol. 1999, No. 09, for JP 11100375 (1999).

* cited by examiner

Primary Examiner—Shailendra Kumar
(74) Attorney, Agent, or Firm—David R. Crichton

(57) ABSTRACT

A process for the preparation of a mixture comprising a compound of formula (1) and a compound of formula (2)

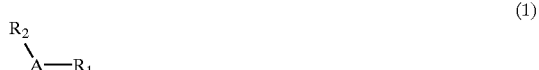

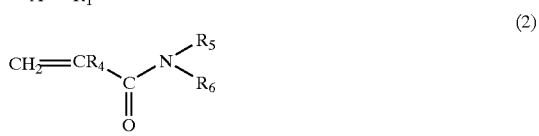

wherein $R_1$ is an optionally substituted $C_{1-20}$ alkyl, optionally substituted $C_{3-4}$ alkenyl, optionally substituted $C_{5-7}$ cycloalkyl or optionally substituted benzyl, $R_2$ is an optionally substituted $C_{1-20}$ alkyl, optionally substituted $C_{3-4}$ alkenyl or optionally substituted $C_{5-7}$ cycloalkyl, A is either S or $NR_3$, $R_3$ is an optionally substituted $C_{1-20}$ alkyl, optionally substituted $C_{3-4}$ alkenyl or optionally substituted $C_{5-7}$ cycloalkyl, or $R_2$ and $R_3$ together form a 5–7 membered ring which can contain an oxygen atom, $R_4$ is hydrogen or methyl, $R_5$ is an optionally substituted $C_{1-20}$ alkyl, optionally substituted $C_{3-4}$ alkenyl, optionally substituted $C_{5-7}$ cycloalkyl or optionally substituted benzyl and, $R_6$ is hydrogen or an optionally substituted $C_{1-20}$ alkyl, optionally substituted $C_{3-4}$ alkenyl or optionally substituted $C_{5-7}$ cycloalkyl, or $R_5$ and $R_6$ together form a 5–7 membered ring which can contain an oxygen atom, which comprises reacting in an alkaline or base medium a compound of formula (3)

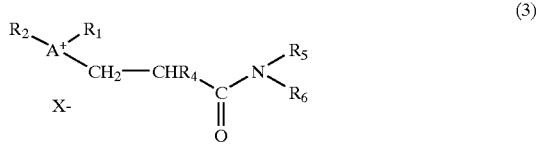

wherein $X^-$ is an anion, $R_1$, $R_2$, $R_3$, $R_4$, $R_5$ and $R_6$ have the same meaning as above, $A^+$ is $S^+$ or $N^+R_3$.

21 Claims, No Drawings

PRODUCTION OF ACRYLIC MONOMERS

This application is a 371 of PCT/EP00/00162 filed Jan. 12, 2000.

The present invention relates to a new synthetic process for producing N-substituted acrylamides and tertiary amines, for instance dialkylallylamine or triallylamine. Substituted acrylamides such as N,N-dimethylacrylamide can be polymerised optionally with other monomers to produce polymers useful as adhesives, fabric sizes and shale inhibitors etc. Allyl dialkyl amines such as allyldimethylamine can be salified or quaternised to produce water soluble monomers which can form water soluble polymers. An important use of allyl dialkyl amines is in the preparation of diallyl-dialkyl ammonium chloride which is commonly used to produce water soluble cationic polymers useful in coagulation and flocculation of solids in suspensions such as sewage sludge or paper making stock suspensions.

It is known to prepare N-substituted acrylamides from acid chlorides such as 3-chloropropionyl chloride. Typically the reaction would be carried out at temperatures between 0° C. and 50° C. A disadvantage of this particular route is the corrosive nature of the acid chlorides, and their high reactivity which can lead to various undesirable side products. It is also known to produce N-substituted acrylamides by pyrolysis of the corresponding aminoalkylamides in the presence of a suitable catalyst. Such processes are carried out at high temperatures, often above 150° C.

One problem with the prior art processes is the occurrence of side reactions which result in lower yields and undesirable impurities which if not removed can adversely affect the properties of the corresponding polymers. On a commercial scale it is often difficult to obtain good yields of N-substituted acrylamides greater than 95% purity.

Another problem with the prior processes is that at such high temperatures it is often necessary to use greater amounts of polymerisation inhibitors. However, the residual inhibitors would need to be removed once the process is complete. Insufficient levels of inhibitor could result in the substituted acrylamide undesirably forming polymers. Furthermore at these high temperatures there is always the risk that free radical species result in the formation of dimers. Even quite low concentrations of dimers or low molecular weight polymer species in the N-substituted acrylamide monomer could be disadvantageous and adversely affect the polymerisation reaction and thus the properties of the final polymer product.

For the reasons set out above it would be desirable to use a process that may if required be carried out at more ambient temperatures and which could be used to prepare N-substituted acrylamides of high purity, for instance above 96% and preferably at least 97%. Furthermore it would also be desirable to use a process that avoids the use of corrosive acid chlorides.

One aspect of the invention relates to a process for the preparation of a mixture comprising a compound of formula (1) and a compound of formula (2)

(1)

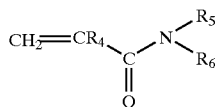

wherein
$R_1$ is an optionally substituted $C_{1-20}$ alkyl, optionally substituted $C_{3-4}$ alkenyl, optionally substituted $C_{5-7}$ cycloalkyl or optionally substituted benzyl,
$R_2$ is an optionally substituted $C_{1-20}$ alkyl, optionally substituted $C_{3-4}$ alkenyl or optionally substituted $C_{5-7}$ cycloalkyl,
A is either S or $NR_3$
$R_3$ is an optionally substituted $C_{1-20}$ alkyl, optionally substituted $C_{3-4}$ alkenyl or optionally substituted $C_{5-7}$ cycloalkyl, or $R_2$ and $R_3$ together form a 5–7 membered ring which can contain an oxygen atom,
$R_4$ is hydrogen or methyl,
$R_5$ is an optionally substituted $C_{1-20}$ alkyl, optionally substituted $C_{3-4}$ alkenyl, optionally substituted $C_{5-7}$ cycloalkyl or optionally substituted benzyl and,
$R_6$ is hydrogen or an optionally substituted $C_{1-20}$ alkyl, optionally substituted $C_{3-4}$ alkenyl or optionally substituted $C_{5-7}$ cycloalkyl, or $R_5$ and $R_6$ together form a 5–7 membered ring which can contain an oxygen atom,
which comprises reacting a compound of formula (3)

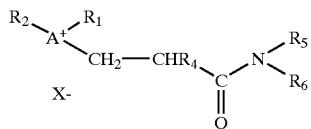

wherein $X^-$ is an anion, and $R_1$, $R_2$, $R_3$, $R_4$, $R_5$ and $R_6$ have the same meaning as above,
in an alkaline medium.

In a preferred form of invention A is $NR_3$ and the compound of formula (1) is specifically a tertiary amine.

In one embodiment $R_1$ is allyl or methallyl.

In one embodiment $R_2$ is methyl or ethyl.

In another embodiment $R_3$ is methyl or ethyl.

In a further embodiment $R_5$ is $C_{1-8}$ alkyl but is preferably selected from methyl, ethyl, n-propyl, iso-propyl, n-butyl and tertiary butyl.

In one other embodiment $R_6$ is hydrogen or $C_{1-8}$ alkyl but is preferably selected from methyl, ethyl, n-propyl, iso-propyl, n-butyl and tertiary butyl and $X^-$ is a halide, preferably chloride.

In a preferred embodiment of the invention $R_1$ is allyl, $R_2$ is methyl or ethyl, $R_3$ is methyl or ethyl, $R_5$ is $C_{1-8}$ alkyl but is preferably selected from methyl, ethyl, n-propyl, iso-propyl, n-butyl and tertiary butyl, $R_6$ is hydrogen or $C_{1-8}$ alkyl but is preferably selected from methyl, ethyl, n-propyl, iso-propyl n-butyl and tertiary but, $X^-$ is preferably a halide, most preferably chloride.

According to the invention the mixtures of compounds of formula (1) and compound of formula (2) can conveniently be prepared by reacting a compound of formula (3) in the presence of a base or an alkali, such as an amine, metal oxide, metal hydroxide or ammonium hydroxide, for instance tertiary amine and/or hindered secondary amine, preferably sodium hydroxide, potassium hydroxide or calcium hydroxide. The reaction may be carried out in an aqueous medium at a pH greater than 8, preferably in the range 11 to 14. In one example the reaction is carried out at a temperature of up to 100° C., preferably 10 to 30° C. Desirably this can be achieved by addition of solid sodium hydroxide or other solid alkali metal hydroxides to the compound of formula (3). It is also possible to effect the elimination by adding an alkali solution, for example caustic soda solution. The alkali solution can be any alkali solution. The alkali is often above 10% strength preferably above 20%, more preferably above 30%, most preferably above 40%, for instance 46%.

Examples of compounds of formula (1) include allyldimethylamine, allyl diethylamine, allyl ethylmethylamine, dimethyl sulphide, allyl methyl sulphide and allyl ethyl sulphide.

Examples of compounds of formula (2) include N-methyl acrylamide, N-ethylacrylamide, N-n-propylacrylamide or N-isopropylacrylamide, N-methylmethacrylamide, N-ethylmethacrylamide, N-n-propylmethacrylamide, N-(2-ethylhexyl)acrylamide or N,N-dimethylacrylamide, N,N-diethylacrylamide, N,N-di n-propylacrylamide, N,N-di iso-propylacrylamide or N,N-dioctyl acrylamide, N-ethyl-N-methylacrylamide, N-methyl-N-propylacrylamide.

Examples of typical mixtures include allyldimethylamine with N-methyl acrylamide, allyldimethylamine with N-ethylacrylamide, allyldimethylamine with n-propylacrylamide, allyldimethylamine with N-isopropylacrylamide, allyldimethylamine with N-methylmethacrylamide, allyldimethylamine with N-ethylmethacrylamide, allyldimethylamine with N-n-propylmethacrylamide, allyldimethylamine with N-(2-ethylhexyl)acrylamide, allyldimethylamine with N,N-dimethylacrylamide, allyldimethylamine with N,N-diethylacrylamide, allyldimethylamine with N,N-di n-propylacrylamide, allyldimethylamine with N,N-di iso-propylacrylamide, allyldimethylamine with N,N-di octyl acrylamide, allyldimethylamine with N-ethyl-N-methylacrylamide, allyldimethylamine with N-methyl-N-propylacrylamide, allyldiethylamine with N-methyl acrylamide, allyldiethylamine with N-ethylacrylamide, allyldiethylamine with n-propylacrylamide, allyldiethy-lamine with N-isopropylacrylamide, allyldiethylamine with N-methylmethacrylamide, allyldiethylamine with N-ethylmethacrylamide, allyldiethylamine with N-n-propylmethacrylamide, allyldiethylamine with N-(2-ethylhexyl)acrylamide, allyldiethylamine with N,N-dimethylacrylamide, allyldiethylamine with N,N-diethylacrylamide, allyldiethylamine with N,N-di n-propylacrylamide, allyldiethylamine with N,N-di iso-propylacrylamide, allyldiethylamine with N,N di octyl acrylamide, allyldiethylamine with N-ethyl-N-methylacrylamide, allyldiethylamine with N-methyl-N-propylacrylamide, allyldimethylamine with N-methyl acrylamide, allyldimethylamine with N-ethylacrylamide, allyldimethylamine with n-propylacrylamide, allylethylm-ethylamine with N-isopropylacrylamide, allylethylmethy-lamine with N-methylmethacrylamide, allylethylmethy-lamine with N-ethylmethacrylamide, allylethylmethylamine with N-n-propylmethacrylamide, allylethylmethylamine with N-(2-ethylhexyl)acrylamide, allylethylmethylamine with N,N-dimethylacrylamide, allylethylmethylamine with N,N-diethylacrylamide, allylethylmethylamine with N,N di n-propylacrylamide, allylethylmethylamine with N,N di iso-propylacrylamide, allylethylmethylamine with N,N di octyl acrylamide, allylethylmethylamine with N-ethyl-N-methylacrylamide, allylethylmethylamine with N-methyl-N-propylacrylamide. The most preferred mixture comprises N,N-dimethylacrylamide with allyldimethylamine.

In one preferred aspect of the invention the compounds of formula (1) and (2) are separated from the mixture by a distillation process. Since the compounds of formula (1) would tend to have a much lower boiling point than the compounds of formula (2) it would be normal to separate the compounds of formula (1) first. However, depending upon the relative boiling points of the two compounds with respect to the boiling point of the solvent one can choose any appropriate conditions for distilling off each of the fractions. Desirably this would be at temperatures up to 120° C., preferably in the range 60–100° C., more preferably 70–90° C. Thus a process for recovering a compound of formula (1) is provided and a process for recovering a compound of formula (2) is provided.

It is also possible to separate compounds (1) and (2) when compound (1) is an amine by addition of a strong acid to the mixture to form a non-volatile salt of the amine, which facilitates removal of compound (2) from the acidified mixture by distillation. Compound (1) can then be regenerated from its salt with strong inorganic base and isolated by distillation, extraction and the like.

Many substituted acrylamides are solids, for instance N-isopropylacrylamide, N-tertiary butylacrylamide, and these can easily be filtered off either before or after removal of compound (1) depending upon the individual properties of the compounds.

As mentioned earlier in the specification the compound of formula (3) can easily be prepared using the novel process disclosed herein. The compound of formula (3) is prepared by reacting compound of formula (4) with compound of formula (5)

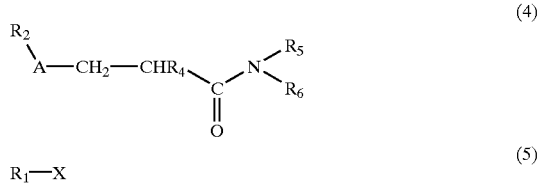

wherein the substituents have the same meaning as defined above. The reaction can be carried out in the presence of any suitable solvent. Ideally the solvent is water, but it is possible to carry out the reaction in any protic solvent such as methanol or polyethylene glycol and in many aprotic solvents such as acetone and dimethylformamide. It is usual to carry out the process at a temperature of up to 100° C., preferably 35–45° C.

Examples of making suitable compounds of formula (3) include the reaction of allyl chloride, methallyl chloride, allyl bromide, dimethyl sulphate or benzyl chloride with any of NN-dimethyl-3-(dimethylamino) propanamide, NN-dimethyl-3-(diethylamino)-propanamide, N-(n-propyl)-3-(dimethylamino)-propanamide, NN-diethyl-3-(dimethylamino)-propanamide, N-iso-propyl-3-(diethylamino)-propanamide, N-N-(n-octyl)-3-(diethylamino)-propanamide, N-ethenyl-3-(dimethylamino)-propanamide, NN-diethylhexyl-3-(diethylamino)-propanamide, NN-diethyl-3-(dimethylamino)-2-methylpropanamide, NN-dimethyl-3-(methylmercapto) propanamide, N-(n-propyl)-3-(methylmercapto)-propanamide. A preferred reaction is between allyl chloride and N,N-dimethyl-3-(dimethylamino)-propanamide.

The invention encompasses a method for the synthesis of a mixture of compounds of formula (1) and (2) by a two step process. The compounds of formula (4) and (5) are reacted in a suitable solvent, for example water and at a temperature of up to 100° C., preferably 35 to 45° C. and then the intermediate of formula (3) that results from this step is reacted under alkaline conditions at a temperature of up to 100° C., preferably 10–30° C. to provide the mixture of compounds of formula (1) and (2).

In a more preferred embodiment of the invention the compound of formula (4) can be prepared by the reaction of an alkyl ester of (meth) acrylic acid with either a sulphide of formula (8) or preferably an amine of formula (6) at a temperature of below 100° C., preferably below 30° C. in order to effect Michael addition of the amine across the double bond. Desirably the alkyl ester of (meth) acrylic acid is methyl (meth) acrylate. Desirably a stoichiometric quantity of either the amine of formula (6) or sulphide of formula (8) is reacted with the alkyl ester of (meth) acrylic acid, the amine of formula (7) maybe reacted at temperatures in excess of 20° C. often in excess of 40° C. often in aprotic solvent and usually in the presence of a suitable amidation catalyst. This reaction converts the ester into the corresponding amide thus liberating the corresponding alkanol, which in the case of methyl (meth) acrylate will be methanol. Other ethylenically unsaturated carboxylic acid esters may be used in place of methyl (meth) acrylate, for instance ethyl acrylate, which would result in the liberation of ethanol.

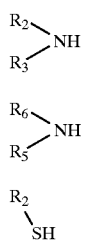

Wherein $R_2$, $R_3$, $R_5$ and $R_6$ are as defined before.

For instance methyl acrylate can be reacted with a molar equivalent of dimethylamine at a temperature of 30° C. The product of this reaction can then be reacted with a stoichiometric equivalent of n-propylamine at a temperature of 40° C.

Diethylamine may also be substitued for dimethylamine or ethyl mercaptan. It is possible to use other amines in place of n-propylamine, for instance, methylamine, dimethylamine, ethylamine, dimethylamine, n-octylamine and piperazine.

All of these amines are known or can be prepared according to known processes.

The invention also encompasses a process of producing a compound of formula (1)

wherein
$R_1$ is an optionally substituted $C_{1-20}$ alkyl, $C_{3-4}$ alkenyl, optionally substituted $C_{5-7}$ cycloalkyl or optionally substituted benzyl,
$R_2$ is an optionally substituted $C_{1-20}$ alkyl, $C_{3-4}$ alkenyl or optionally substituted $C_{5-7}$ cycloalkyl,
A is either S or $NR_3$, and
$R_3$ is an optionally substituted $C_{1-20}$ alkyl, $C_{3-4}$ alkenyl or optionally substituted $C_{5-7}$ cycloalkyl, or $R_2$ and $R_3$ together form a 5–7 membered ring which can contain oxygen.

by the following steps
1) reaction of an alkyl ester of (meth) acrylic acid, for instance methyl (meth) acrylate first with a sulphide of formula (8) or preferably an amine of formula (6) at a temperature of below 100° C., preferably below 50° C., more preferably below 30° C. in order to effect Michael addition of the amine across the double bond.
2) Once a stoichiometric quantity of the sulphide of formula (8) or amine of formula (6) has been reacted with the alkyl ester of (meth) acrylic acid the amine of formula (7) may be reacted at temperatures in excess of 20° C. often in excess of 40° C., often in a protic solvent and usually in the presence of a suitable amidation catalyst. This reaction converts the ester into the corresponding amide thus liberating methanol and forming the compound of formula (4)

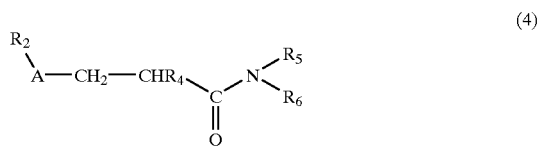

wherein
$R_2$ is an optionally substituted $C_{1-20}$ alkyl, $C_{3-4}$ alkenyl or optionally substituted $C_{5-7}$ cycloalkyl,
A is either S or $NR_3$,
$R_3$ is an optionally substituted $C_{1-20}$ alkyl, $C_{3-4}$ alkenyl or optionally substituted $C_{5-7}$ cycloalkyl, or $R_2$ and $R_3$ together form a 5–7 membered ring which can contain oxygen.
$R_4$ is hydrogen or methyl,
$R_5$ is an optionally substituted $C_{1-20}$ alkyl, $C_{3-4}$ alkenyl, optionally substituted $C_{5-7}$ cycloalkyl or optionally substituted benzyl or
$R_6$ is hydrogen or an optionally substituted $C_{1-20}$ alkyl, $C_{3-4}$ alkenyl or optionally substituted $C_{5-7}$ cycloalkyl or $R_5$ and $R_6$ together form a 5–7 membered ring which can include an oxygen atom.
3) The compound of formula (4) is reacted with the compound of formula (5)

wherein
$R_1$ is an optionally substituted $C_{1-20}$ alkyl, $C_{3-4}$ alkenyl, optionally substituted $C_{5-7}$ cycloalkyl or optionally substituted benzyl, preferably allyl or methallyl and X is an atom or moiety that is capable of forming an anion, preferably a halide, most preferably chloride. The compounds of formula (4) and (5) are reacted in a suitable solvent, for example water and at a temperature of up to 100° C., preferably 35 to 45° C. to form the intermediate of formula (3)

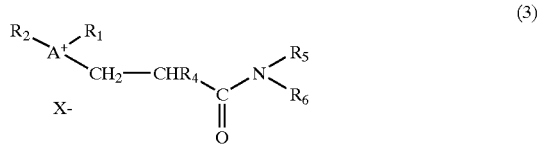

wherein $A^+$ is either $S^+$ or $N^+R_3$ and $R_1$ to $R_6$ are defined above and $X^-$ is an anion, preferably halide, especially chloride.

4) Compound (3) is reacted under alkaline conditions at a temperature of up to 100° C., preferably 10 to 30° C. to provide the mixture of compounds of formula (1) and (2).

(1)

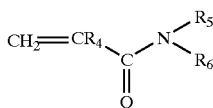
(2)

5) The compounds of formula (1) and (2) can be separated from the mixture, by solvent extraction or preferably by a distillation process. The compound of formula (1) can easily be separated from the mixture comprising compounds (1) and (2) and water, if the boiling points of compounds (1) and (2) and water are well separated and (1) and (2) do not form azeotropic mixtures. Often the compound has a lower boiling point that the compound (2). Therefore compound (1) can normally be separated from the mixture by a distillation process. Normally the separated compound (1) is obtained in pure form. However, it may be necessary to carry out a further purification step in order to remove any residual compound (2). This purification step may for instance include washing with a suitable solvent for the compound of formula (2), which is not a solvent for the compound of formula (1). Often the compound of formula (1) would be obtained in subtantially pure form without the need for further purification.

Typical examples of compounds of formula (1) include allyldimethylamine, allyldiethylamine and allyl methyl sulphide. A typical use of compounds of formula (1) would be either to form the corresponding polymers, optionally with other monomers. Typically copolymers of allyldimethylamine with acrylamide can be used as flocculants in avarty of industries. Another more important use of a compound of formula (1) is in the preparation of diallyldialkylammonium halide by reaction of compound (1) with allyl chloride. Typically diallyldimethylammonium chloride (DADMAC) can be prepared by reacting allyldimethylamine with allyl chloride. DADMAC is a well known monomer that can be homopolymerised to form low molecular weight cationic polymers, suitable as coagulants for solids liquids separation. Alternatively DADMAC can be copolymerised with acrylamide to form higher molecular weight cationic polymers which are suitable for use as flocculants.

The invention further encompasses a process of producing a compound of formula (2)

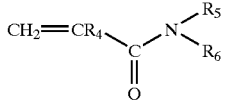
(2)

wherein $R_4$ is hydrogen or methyl, $R_5$ is an optionally substituted $C_{1-20}$ alkyl, $C_{3-4}$ alkenyl, optionally substituted $C_{5-7}$ cycloalkyl or optionally substituted benzyl, $R_6$ is hydrogen or an optionally substituted $C_{1-20}$ alkyl, $C_{3-4}$ alkenyl or optionally substituted $C_{5-7}$ cycloalkyl, or $R_5$ and $R_6$ together form a 5–7 membered ring which can contain an oxygen atom, by the following steps 1) reaction of an alkyl ester of (meth) acrylic acid, for instance alkyl ester of (meth) acrylic acid, preferably methyl acrylate first with a sulphide of formula (8) or preferably an amine of formula (6) at a temperature of below 100° C., preferably below 50° C., more preferably below 30° C. in order to effect Michael addition of the amine across the double bond.

2) Once a stoichiometric quantity of the sulphide of formula 8) or amine of formula (6) has been reacted with the alkyl ester of (meth) acrylic acid, the product of the reaction is reacted with the amine of formula (7) at temperatures in excess of 20° C. often in excess of 40° C., optionally with a protic solvent, preferably methanol and with an amidation catalyst, preferably sodium methoxide or dibutyl tin oxide. This reaction converts the ester into the corresponding amide thus liberating the corresponding alkanol and forming the compound of formula (4)

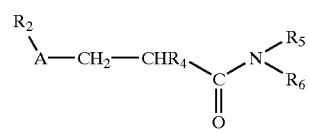
(4)

wherein $R_2$ is an optionally substituted $C_{1-20}$ alkyl, $C_{3-4}$ alkenyl or optionally substituted $C_{5-7}$ cycloalkyl, A is S or $NR_3$, $R_3$ is an optionally substituted $C_{1-20}$ alkyl, $C_{3-4}$ alkenyl or optionally substituted $C_{5-7}$ cycloalkyl, or $R_2$ and $R_3$ together form a 5–7 membered ring which can contain oxygen.

$R_4$ is hydrogen or methyl, $R_5$ is an optionally substituted $C_{1-20}$ alkyl, $C_{3-4}$ alkenyl, optionally substituted $C_{5-7}$ cycloalkyl, or optionally substituted benzyl and, $R_6$ is hydrogen or an optionally substituted $C_{1-20}$ alkyl, $C_{3-4}$ alkenyl or optionally substituted $C_{5-7}$ cycloalkyl or $R_5$ and $R_6$ together form a 5–7 membered ring which can contain oxygen.

3) The compound of formula (4) is reacted with the compound of formula (5)

(5)

wherein $R_1$ is an optionally substituted $C_{1-20}$ alkyl, $C_{3-4}$ alkenyl, optionally substituted $C_{5-7}$ cycloalkyl or optionally substituted benzyl, preferably allyl or methallyl and X is an atom or moiety that is capable of forming an anion, preferably a halide, most preferably chloride. The compounds of formula (4) and (5) are reacted in a suitable solvent, for example water and at a temperature of up to 100° C., preferably 35–45° C. to form the intermediate of formula (3)

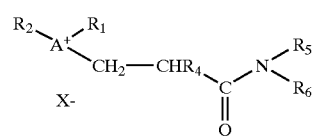
(3)

wherein $A^+$ and $R_1$ to $R_6$ are as defined above and $X^-$ is an anion, preferably halide especially chloride.

4) Compound (3) is reacted under alkaline conditions at a temperature of up to 100° C., preferably 10 to 30° C. to provide the mixture of compounds of formula (1) and (2).
5) The compounds of formula (1) and (2) can often be separated from the mixture by a distillation process. The compound of formula (1) can easily be separated from the mixture comprising compound (1) and compound (2) and water, if the boiling points of compounds (1) and (2) and water are well separated and (1) and (2) do not form azeotropic mixtures. Usually the compound of formula (1) will have a lower boiling point than the compound of formula (2). The compound of formula (1) can therefore normally be removed from the mixture by a distillation process. Normally the separated compound of formula (2) is obtained in pure form. However, it may be necessary to carry out a further purification step in order to remove any residual compound of formula (1). This purification step may for instance include washing with a suitable solvent for the compound of formula (1), which is not a solvent for the compound of formula (2). Often the compound (1) can easily an effectively be obtained in subtantially pure form without the need for further purification.

Compounds of formula (2) are typically N-substituted or N,N-disubstituted acrylamides. Typically such compounds include N-methyl acrylamide, N-ethylacrylamide, N-n-propylacrylamide or N-isopropylacrylamide N-methylmethacrylamide, N-ethylmethacrylamide, N-n-propylmethacrylamide, N-(2-ethylhexyl)acrylamide, N,N-dimethylacrylamide, N,N-diethylacrylamide, N,N-di n-propylacrylamide, N,N di iso-propylacrylamide or N,N di octyl acrylamide N-ethyl-N-methylacrylamide, N-methyl-N-propylacrylamide. Typically such compounds can be polymerised optionally with other monomers to produce polymers useful as surface coatings for wood or for paper, adhesives, fabric sizes and shale inhibitors etc.

The invention provides a convenient process for the synthesis of a mixture of compounds (1) and (2) starting from commercially available material that can be conducted at moderate temperatures and it avoids the use of corrosive chemicals such as acid chlorides. Another advantage of the invention is the synthesis of the N-substituted acrylamides of formula (2), simultaneously with another commercially useful compound. The invention also surprisingly allows the compounds of formula (1) and formula (2) to be made in high yield and at a very high purity. In particular we have surprisingly found that N-substituted acrylamides, for instance N,N-dimethylacrylamide can be synthesized on a commercial scale, for instance in commercial quantities to a purity greater than 96%.

The following examples illustrate the invention but are not intended to limit the scope of invention.

EXAMPLE 1

Preparation of N,N-Dimethyl-3-dimethylaminopropanamide

Methyl acrylate 430 g and methanol 430 g are stirred together in a flask and dimethylamine gas is passed into the mixture. The reaction is exothermic and cooling is applied to the mixture to keep the reaction temperature to below 35° C. When 495 g of dimethylamine have been added 30% sodium methoxide catalyst 45 g is added resulting in temperature rise from 25° C. to 33° C.

Once complete amidation has occurred 36% hydrochloric acid 25 g or 98% sulphuric acid 12.5 g is added to neutralise the sodium methoxide.

Methanol and excess dimethylamine are removed by distillation, initially at atmospheric pressure and finally under reduced pressure at 40 to 50° C. to give N,N-dimethyl-3-dimethylaminopropanamide containing sodium chloride or sodium sulphate as a suspended solid which can be removed by filtration.

EXAMPLE 2

Preparation of the Allyl Chloride Quaternary Salt of N,N-Dimethyl-3-dimethylaminopropanamide Allyl chloride 382.5 g and water are stirred together and warmed to 35° C. N,N-dimethyl-3-dimethylaminopropanamide 710 g is added over about 2 hours. The reaction is exothermic and so cooling is required to keep the temperature in the range 35 to 45° C. The resulting viscous solution of the allyl chloride quaternary salt of NN-dimethyl-3-dimethylaminopropanamide is stirred for a further hour and cooled to 20 to 25° C.

EXAMPLE 3

Preparation of Allyldimethylamine and N,N-Dimethylacrylamide

Pearl caustic soda 200 g is added with stirring to the allyl chloride quaternary salt of NN-dimethyl-3-dimethylaminopropanamide from example 2. The reaction rises slowly to 31° C. and then falls back to 25° C. as the reaction proceeds. The resulting mixture contains sodium chloride which is filtered off. Any excess soda can be neutralised by addition of 36% HCl (about 5 g) before distillation.

EXAMPLE 4

Separation of Allyldimethylamine and N,N-Dimethylacylamide from the Reaction Product of Example 3

The mixture is distilled using a 6 inch long, 1 inch diameter glass column packed with 3/16-inch stainless steel Raschig rings. The column top is fitted with a reflux to take-off splitter. Allyldimethylamine (ADMA) is distilled out under atmospheric pressure at a temperature of 59 to 63° C. to effect boiling of the ADMA as an azeotrope with water (96% ADMA, 4% water). The liquid temperature is taken to 100° C. and a slight vacuum is applied to ensure virtually complete removal of ADMA. The latter part of the distillation process requires a high reflux.

The remaining mixture is cooled to 50° C. and the pH is adjusted to 6 with 36% HCl. A vacuum is applied and a middle fraction bp 38 to 55° C./50 mb consisting of mainly water with some dimethylacrylamide is collected. High reflux to take-off ratio is required to give good separation.

When the distillation temperature starts to rise rapidly, the receiver is changed and NN-dimethylacrylamide bp 80° C./25 mb is collected at full take-off. Yields are shown in Table 1.

TABLE 1

| Fraction | Quantity | Analysis |
|---|---|---|
| 1 | 350 g | GC Analysis shows: 99.9% ADMA by area 96% vs standard (anhydrous) 99.1 by titration KF 4–5% water |

TABLE 1-continued

| Fraction | Quantity | Analysis |
| --- | --- | --- |
| 2 | about 250 g | KF 88% water<br>GC 12% NN-dimethylacrylamide |
| 3 | 390 g | GC analysis shows:<br>99.4% NN-dimethylacrylamide<br>98.1% vs standard<br>KF 0.22% water |

Overall yield of allyldimethylamine from methyl acrylate 82%
Overall yield of dimethylacrylamide from methyl acrylate 77%.

EXAMPLE 5

Preparation of Allyldimethylamine and NN-Dimethylacrylamide Using 46% Caustic Soda Solution 46% caustic soda solution (435 g) is added with stirring to the allyl chloride quaternary salt of NN-dimethyl-3-dimethylaminopropanamide from example 2. Addition is carried out over one hour and the temperature falls during this time from 23° C. to 14° C. as the reaction proceeds. The pH of the reaction mixture is between 12 and 14.

Extra 46% caustic soda solution (220 g) is quickly added causing separation of an upper organic layer (995 g) to which is added a little 36% hydrochloric acid to neutralise any residual caustic soda.

The organic layer is distilled as in example 4 to give 353 g of ADMA (99.9% ADMA area, 96% vs standard (anhydrous), KF—4% water. A middle fraction (225 g containing 10% NN dimethylacrylamide (406 g) distils (GC 99.4% NN-dimethylacrylamide vs standard KF—0.22% water).

Example 6

Preparation of 3-(4-Morpholino)-Propionyl-Morpholine

A solution of 346 g of methyl-3-(4-morpholino) propionate in methanol (162 g) is stirred and morpholine (174 g) is added, followed by 20 g of 30% methanofic sodium methoxide. The mixture is warmed to 65–70° C. and kept 5 hours at this temperature, when GC analysis indicates complete reaction. 36% hydrochloric acid (11.2 g) is added slowly to neutralise sodium methoxide and the cooled mixture is distilled under reduced pressure to remove methanol and the residue treated with acetone, filtered, and the solid washed acetone. The solid is dried at 50° C. to give 336 g of 3-(4-morpholino)propionyl-morpholine as a colourless solid melting point 98–100° C.

EXAMPLE 7

Preparation of 1-Methylmorpholine and Acrylamidomorpholine

A solution of 3-(4-morpholino)-propionyl morpholine (350 g) in water (200 g) is stirred and dimethyl sulphate (200 g) is added dropwise with cooling to keep the temperature below 30° C. The mixture is stirred for a further 2 hours at 30° C. and then 46% caustic soda solution (139 g) added slowly over 1 hour. A further 139 g of 46% caustic soda solution is added causing separation of an upper layer. GC analysis of the organic layer shows the presence of 1-methyl morpholine (119 g) and acrylamido morpholine (171 g), which are easily separated by distillation boiling points 116° C. (1000 mb) and 80–84° C. (2 mb) respectively.

EXAMPLE 8

Preparation of N,N'-bis-3(4-Morpholino)propionyl Piperazine

A solution of 346 g of methyl-3-(4-morpholino) propionate in methanol (162 g) is stirred as piperazine (86 g) and 30% methanolic sodium methoxide solution (20 g) is added. The reaction mixture is left 48 hours at ambient temperature and then filtered and the solid washed with cold methanol. The material is dried at 60° C. to give NN'-bis-3-(4-morpholino)propionyl piperazine as a colourless crystaline solid MP 145–146° C., yield 224 g.

EXAMPLE 9

Preparation of 1-Methylmorpholine and N,N'-Bis-Acrylamidopiperazine

A solution of 200 g of NN'-bis-3(4-morpholino-propionyl piperazine in water (220 g) is stirred and cooled as dimethyl sulphate (137 g) is added keeping the temperature below 35° C. The mixture is stirred for a further 2 hours to give a clear solution pH 6.5.

46% caustic soda solution (94.4 g) is now added slowly with stirring and then para-methoxy phenol (0.5 g) added and the azeotrope of 1-methylmorpholine and water Bp 94° C. (1000 mb) is distilled out (121 g, containing 29 g of water and 92 g of 1-methyl morpholine). The resulting solution is extracted several times with methyl ethyl ketone. The solvent extracts are evaporated, leaving 70 g of NN'-bis-acrylamidopiperazine, as a white crystaline solid, mp 95–97° C.

EXAMPLE 10

Preparation of 3-Dimethylamino-N-iso-Propylpropanamide

Methyl-3-dimethylaminopropionate (131 g) is stirred as isopropylamine (71 g) as added followed by 30% methanolic sodium methoxide solution (18 g). After 3 days at ambient temperature, GC analysis indicated 98% conversion. Excess isopropylamine is evaporated off under reduced pressure leaving 3-dimethylamino-N-isopropylpropanamide (155 g) as a pale yellow oil.

EXAMPLE 11

Preparation of Allyldimethylamine and N-Isopropyl Acrylamide

3-Dimethylamino-N-isopropylpropanamide (155 g) prepared as in example 10 is dissolved in acetone (220 ml) and allyl chloride (90 g) is added slowly with stirring at 35–40° C. The mixture is cooled to 20° C. and 46% caustic soda solution (87 g) is added slowly with stirring, and stirred for 2 hours. Sodium chloride is filtered off leaving a pale yellow solution (390 g).

Analysis of the solution by GC shows it to contain 92 g of N-isopropylacrylamide and 42 g of allyldimethylamine.

EXAMPLE 12

Preparation of N-(3-TrimethylAmmonium) Propyl Acrylamide Chloride and Trimethylamine N-(3dimethylamino)propyl-3-dimethylaminoethyl propanamide (26.3 g) is added to a solution of methyl chloride (22.5 g) in acetone (24.8 g) and the mixture is left to stand at ambient temperatures for 48 hours. Acetone is decanted from the crystalline residue which is dissolved in water (50 ml). 46% caustic soda solution (11.4 g) is added slowly to the aqueous solution, which is left for 2 hours at 20–25° C. and then analysed by ion chromatography. This shows the solution contains 17.2 g of N-(3-trimethylammonium)-propylacrylamide chloride. GC confirms the presence of trimethylamine.

EXAMPLE 13

Preparation of 3-Dimethylamino-2-Methyl-N-Isopropylpropanamide

Methyl-3-dimethylamino-2-methyl propionate (299 g, prepared by Michael addition of 1 equivalent of dimethylamine to methyl methacrylate) and methanol (300 ml) are stirred as isopropylamine (177 g) is added, followed by 35 g of 30% methanolic sodium methoxide solution. The reaction mixture is warmed to 70° C. for 16 hours when GC analysis indicates greater than 90% conversion to the amide.

The solution is cooled to 20° C. and 36% hydrochloric acid (20 g) is added to neutralise the sodium methoxide. The mixture is filtered to remove salt and methanol and excess isopropylamine removed under reduced pressure to give crude 3-dimethylamino-2-methyl-N-isopropylpropanamide as an off-white solid. Pure product, mp 67–69° C. can be obtained by crystallisation from petroleum spirit (bp 100–120° C.).

EXAMPLE 14

Preparation of Allyl Dimethylamine and N-isopropyl Methacrylamide

A mixture of allyl chloride (76.5 g) and water (50 ml) is stirred at 20° C. and 3-dimethylamino-2-methyl-N-isopropylpropanamide (175 g, prepared in example 13) is added in portions keeping the temperature below 30° C. When addition is complete the mixture is stirred for 16 hours to give a viscous clear solution of allyl chloride quaternary amonium salt 46% caustic soda solution (87 g) is added and the mixture stirred at 20–25° C. for 3–4 hours. During this time N-isopropylmethacrylamide separates as a white crystalline solid, Allyldimethylamine can be recovered by distillation from the reaction mixture. N-isopropyl methacrylamide is recovered by filtration of the mixture remaining after distillation of the allyldimethylamine. The filtered solid is washed with water and dried in air to give N-isopropylmethacrylamide as a crystalline solid mp 89–91° C.

What is claimed is:

1. A process for the preparation of a mixture comprising a compound of formula (1) and a compound of formula (2)

(1)

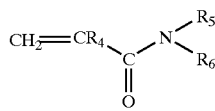

(2)

wherein $R_1$ is allyl or methallyl, $R_2$ is an optionally substituted $C_{1-20}$ alkyl, optionally substituted $C_{3-4}$ alkenyl or optionally substituted $C_{5-7}$ cycloalkyl, A is either S or $NR_3$, $R_3$ is an optionally substituted $C_{1-20}$ alkyl, optionally substituted $C_{3-4}$ alkenyl or optionally substituted $C_{5-7}$ cycloalkyl, or $R_2$ and $R_3$ together form a 5–7 membered ring which can contain an oxygen atom, $R_4$ is hydrogen or methyl, $R_5$ is an optionally substituted $C_{1-20}$, alkyl, optionally substituted $C_{3-4}$ alkenyl, optionally substituted $C_{5-7}$ cycloalkyl or optionally substituted benzyl and, $R_6$ is hydrogen or an optionally substituted $C_{1-20}$ alkyl, optionally substituted $C_{3-4}$, alkenyl or optionally substituted $C_{5-7}$ cycloalkyl, or $R_5$ and $R_6$ together form a 5–7 membered ring which can contain an oxygen atom, which comprises reacting a compound of formula (3)

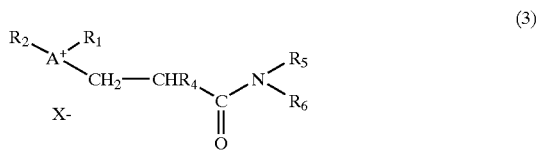

(3)

wherein $X^-$ is an anion, A is either $S^+$ or $N^+R_3$ and $R_1$, $R_2$, $R_3$, $R_4$, $R_5$ and $R_6$ have the same meaning as above, in an alkaline or base medium.

2. A process according to claim 1 in which the compound of formula (1) is first removed from the mixture by a distillation under vacuum at a suitable temperature, optionally followed by purifying to remove residual compound of formula (1) thereby providing the compound in essentially pure form.

3. A process according to claim 1 in which $R_2$ is $C_{1-2}$ alkyl.

4. A process according to claim 1 in which $R_3$ is $C_{1-2}$ alkyl.

5. A process according to claim 1 in which $R_5$ is $C_{1-8}$ alkyl.

6. A process according to claim 1 in which $R_6$ is $C_{1-8}$ alkyl.

7. A process according to claim 1 in which $X^-$ is a halide.

8. A process according to claim 1 in which the compound of formula (3) is reacted with a tertiary amine, hindered secondary amine or an alkali metal oxide, alkali metal hydroxide, alkaline earth metal oxide, alkaline earth metal hydroxide or ammonium hydroxide.

9. A process according to claim 1 in which the reaction is carried out in an aqueous medium at a pH of greater than 8.

10. A process according to claim 1 in which the reaction is carried out at a temperature of up to 100° C.

11. A process according to claim 1 in which the compound of formula (3) is prepared by reacting compound of formula (4) with compound of formula (5)

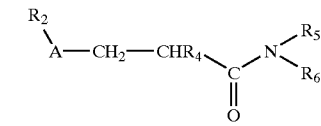

(4)

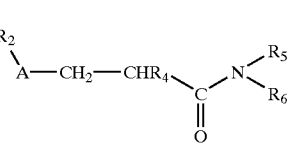

(5)

wherein

X is any atom or molecule capable of forming an anion.

12. A process according to claim 11 in which the compound of formula (4) is reacted with the compound of formula (5) in a solvent at a temperature of up to 100° C.

13. A process according to claim 1 in which after preparation of the mixture of compounds (1) and (2), compounds (1) and (2) are separated.

14. A process according to claim 1 in which compound of formula (3) is prepared by reacting compound of formula (4) with compound of formula (5)

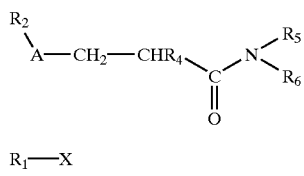

(4)

R1—X (5)

wherein

X is an atom or molecule capable of forming an anion.

15. A process according to claim 14 in which the compound or formula (4) is reacted with the compound of formula (5) in a solvent at a temperature of up to 100° C.

16. A process according to claim 1 comprising the steps, (1) reacting an ethylenically unsaturated carboxylic ester with a sulphide of formula (8) or an amine of formula (6) at a temperature of below 100° C. to effect Michael addition,

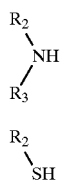

(6)

(8)

(2) reacting the product of step (1) with an amine of formula (7) at a temperature in excess of 20° C. optionally in the presence of a suitable catalyst

(7)

(3) reacting the product of step (2) with a suitable quaternising compound (4) reacting the product of step (3) with a base or an alkali to provide a mixture of compounds of formula (1) and of formula (2).

17. A composition comprising a compound of formula (1) and a compound of formula (2)

(1)

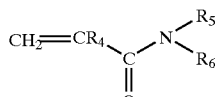

(2)

wherein A and $R_1$ to $R_6$ have the same definition as in claim 1.

18. A process of producing a compound of formula (1)

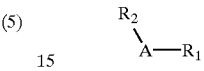

(1)

wherein $R_1$ allyl of methallyl, $R_2$ is an optionally substituted $C_{1-20}$ alkyl, optionally substituted $C_{3-4}$ alkenyl or optionally substituted $C_{5-7}$ cycloalkyl, A is either S or $NR_3$, in which a mixture comprising a compound of formula (1) and a compound of formula (2) is provided according to the steps defined by claim 1, followed by subjecting the mixture to a separation step selected from solvent extraction and distillation.

19. A process according to claim 18 in which the compound of formula (1) is separated from the mixture by a distillation under vacuum at a suitable temperature.

20. A process of producing a compound of formula (2)

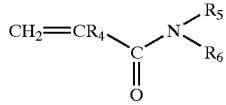

(2)

wherein $R_4$ is hydrogen or methyl, $R_5$ is an optionally substituted $C_{1-20}$ alkyl, optionally substituted $C_{3-4}$ alkenyl, optionally substituted $C_{5-7}$ cycloalkyl or optionally substituted benzyl and, $R_6$ is hydrogen or an optionally substituted $C_{1-20}$ alkyl, optionally substituted $C_{3-4}$ alkenyl or optionally substituted $C_{5-7}$ cycloalkyl, or $R_5$ and $R_6$ together form a 5–7 membered ring which can contain an oxygen atom, in which a mixture comprising a compound of formula (1) and a compound of formula (2) is provided according to the steps defined by claim 1, followed by subjecting the mixture to a separation step selected from solvent extraction and distillation.

21. A process according to claim 20 in which the compound of formula (1) is first removed from the mixture by purifying to remove residual compound of formula (1) thereby providing the compound in essentially pure form.

* * * * *